United States Patent
Bratz et al.

(10) Patent No.: US 6,313,070 B1
(45) Date of Patent: Nov. 6, 2001

(54) STORAGE STABLE AQUEOUS FORMULATIONS BASED ON N-PHENYL-3,4, 5,6-TETRAHYDROPHTHALIMIDE HERBICIDES

(75) Inventors: Matthias Bratz, Limburgerhof; Rainer Berghaus, Speyer; August Wigger, Kemnath-Stadt; Adolf Parg, Bad Dürkheim; Wessel Nuyken, Otterstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/582,883
(22) PCT Filed: Feb. 8, 1999
(86) PCT No.: PCT/EP99/00807
§ 371 Date: Jul. 6, 2000
§ 102(e) Date: Jul. 6, 2000
(87) PCT Pub. No.: WO99/39579
PCT Pub. Date: Aug. 12, 1999

(30) Foreign Application Priority Data

Feb. 7, 1998 (DE) .............................. 198 04 913

(51) Int. Cl.$^7$ ............................. A01N 25/30; A01N 43/38
(52) U.S. Cl. ......................... 504/132; 504/134; 504/138; 504/286; 504/363
(58) Field of Search ................................. 504/132, 134, 504/138, 286, 363

(56) References Cited

U.S. PATENT DOCUMENTS

| | | | |
|---|---|---|---|
| 4,816,065 | * 3/1989 | Theodoridis | 71/94 |
| 5,045,105 | 9/1991 | Grossmann et al. | 71/74 |
| 5,062,884 | 11/1991 | Plath et al. | 71/95 |

FOREIGN PATENT DOCUMENTS

| | | |
|---|---|---|
| 240 659 | 10/1987 | (EP) . |
| 362 639 | 4/1990 | (EP) . |
| 385 231 | 9/1990 | (EP) . |
| 98/07319 | 2/1998 | (WO) . |

OTHER PUBLICATIONS

Heck et al.,Herbizide, 1995, p. 144–145.
Agr.Bio.Chem.55 (11), pp 2677–2681 (1991).
Proc.Brighton Crop Prot. Conf. Weeds 1989, vol. 1, p. 41–51.
Proc.Brighton Crop Prot. Conf. Weeds vol. 1, p. 69–75.
Biosci.Biotec.Biiochem 57 (11) pp 1913–1915 (1993).
Am.Chem.Soc.Symp.Series, 559, pp. 18–33 (1994) Anderson et al.
Pest.Manual.10th Ed. 1994, pp 488 & 489.

* cited by examiner

Primary Examiner—S. Mark Clardy
(74) Attorney, Agent, or Firm—Herbert B. Keil

(57) ABSTRACT

Storage-stable aqueous formulations comprising
  a) 0.1–60% by weight of a tetrahydrophthalimide of the formula I where
$R^1$=H, F, Cl;
$R^2$=CH=C(Cl)—CO—B or CH=C(Br)—CO—B (B=$C_1$–$C_6$-alkyl, unsubstituted or substituted OH or SH);
a group $OR^5$, $SR^5$, $COOR^5$, $OCH_2COOR^5$, $CH_2$—CO—$OR^6$ or ($C_1$–$C_6$-alkyl)sulfonylamino;
$R^5$=H, $C_1$–$C_6$-alkyl, $C_3$–$C_7$-cycloalkyl, $C_2$–$C_8$-alkenyl, $C_2$–$C_6$-alkynyl, ($C_1$–$C_6$-alkoxy)carbonyl-$C_1$–$C_6$-alkyl or $C_1$–$C_6$-alkyloximino-$C_1$–$C_6$-alkyl
$R^3$=Cl, CN;
$R^6$=is H, $C_1$–$C_6$-alkyl, $C_2$–$C_8$-alkenyl, $C_2$–$C_6$-alkynyl, $C_3$–$C_7$-cycloalkyl, $C_1$–$C_6$-alkoxy-$C_1$–$C_6$-alkyl or $C_1$–$C_6$-alkyloximino-$C_1$–$C_6$-alkyl;
  b) 0.1–30% by weight of an anionic surfactant;
  c) 0.1–30% by weight of a non-ionic surfactant;
  d) 0.01–5% by weight of a thixotroping additive;
  e) 0–50% by weight of other herbicidal active ingredients;
  f) 0–20% by weight of other formulation auxiliaries, and
  g) 1–90% of water. Storage-stable aqueous formulations based on N-phenyl- 3,4,5,6 -tetrahydrophthalimide derivatives, and their use as herbicides in crop protection

2 Claims, No Drawings

STORAGE STABLE AQUEOUS FORMULATIONS BASED ON N-PHENYL-3,4,5,6-TETRAHYDROPHTHALIMIDE HERBICIDES

The present invention relates to storate-stable aqueous formulations based on N-phenyl-3,4,5,6-tetrahydrophthalimide derivatives of the formula I and to their use as herbicides in crop protection

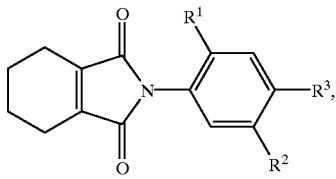

I where the substituents have the following meanings:
R$^1$ is hydrogen, fluorine or chlorine;
R$^2$ is a group A—CO—B where
   A is CH=C(Cl) or CH=C(Br) and
   B is C$_1$–C$_6$-alkyl or a group OR$^4$ or SR$^4$ where
      R$^4$ is hydrogen, C$_1$–C$_4$-alkyl, (C$_1$–C$_6$-alkoxy)carbonyl-C$_1$–C$_6$-alkyl or C$_1$–C$_6$-alkyloximino-C$_1$–C$_6$-alkyl, or
R$^2$ is a group OR$^5$, SR$^5$, COOR$^5$ or OCH$_2$COOR$^5$ where
   R$^5$ is hydrogen, C$_1$–C$_6$-alkyl, C$_3$–C$_7$-cycloalkyl, C$_3$–C$_8$-alkenyl, C$_3$–C$_6$-alkynyl or C$_1$–C$_6$-alkoxy-C$_1$–C$_6$-alkyl, or
R$^2$ is a group CH$_2$—CO—OR$^6$ where
   R$^6$ is C$_1$–C$_6$-alkyl or C$_1$–C$_6$-alkoxy-C$_1$–C$_6$-alkyl, or a group —NHSO$_2$-(C$_1$–C$_6$-alkyl) and
R$^3$ is chlorine or cyano.

Herbicides based on tetrahydrophthalimides of the formula I have been disclosed in the literature, for example in: EP-A 240 659; Herbizide, Heck, B.; Fedtke, C.; R. R. Schmidt; Thieme Stuttgart 1995, p. 144; Proc. Brighton Crop Protection Conference Weeds 1989, Vol. 1, p. 41; Proc. Brighton Crop Protection Conference Weeds 1991, Vol. 1, p. 69; Anderson et al., American Chemical Soc. Symposium Series 559 (1994), 18–33.

It can be seen from the literature that these products are formulated in most cases as solid formulations, for example water-dispersible powders or granules, or as emulsion concentrates, for example flumiclorac (trade name RESOURCE® EC, cf. The Pesticide Manual 10th Edition, p. 488) or flumioxazin (trade name SUMISOYA® WP, cf. The Pesticide Manual 10th Edition, p. 489).

The abovementioned formulations can have a series of disadvantages under practice conditions. Thus, for example, the solvents which the EC formulations (emulsion concentrate) comprise are considered as disadvantageous in the continuing debate about the environment. Moreover, the solvents used entail, as a rule, an inflammability which is not desired. In addition, the limited solubility of the active ingredients limits the preparation of highly-concentrated formulations. In the case of WP formulations (water-dispersible powders), the fact that dust is frequently generated upon use is considered to be disadvantageous.

Formulations in the form of aqueous suspension concentrates should not exhibit the disadvantages described above, but concentrates of this type were as yet unknown for tetrahydrophthalimides.

The reason for this may be the fact that the class of the tetrahydrophthalimides is described in the literature as sensitive to hydrolysis. Thus, it is known from Nippon Noyaku Gakkaishi (1989), 14(4), 497–501 (CA 1990: 215895) that tetrahydrophthalimides are not stable in aqueous systems. The half-lives of tetrahydrophthalimide measured in aqueous systems at pH 5 are 4.14 days and at pH 7 only 9.14 hours.

The lack of stability of derivatives from the class of the tetrahydrophthalimides has also been described in Biosci., Biotechnol., Biochem. (1993), 57(11) 1913–15 and Agric. Biol. Chem. (1991), 55(11), 2677–2678.

EP-A 385 231 discloses the use of certain active ingredients from the class of the tetrahydrophthalimides for the desiccation and abscission of plant organs. This publication mentions that the active ingredients can be employed in the form of various formulations, and a long list also includes highly-concentrated aqueous forms (p. 6, lines 45 et seq.). However, it can be seen from the further details that the aqueous use forms are prepared from emulsion concentrates, pastes or wettable powders, i.e. from use forms which have the disadvantages described at the outset. The starting systems always comprise solvent. EP-A 385,231 thus does not disclose storage-stable aqueous formulations to the expert, but, rather, teaches away from such a use form.

EP-A 240 659 describes certain tetrahydrophthalimides; the formulation details correspond to those in EP 385 231 which has been discussed above.

It is an object of the present invention to develop aqueous storage-stable formulations which do not have the disadvantages described at the outset. In particular, the storage stability should meet the guidelines of the FAO Manual on the development and use of FAO specifications for plant protection products, 44$^{th}$ Edition, Rome, 1992. In accordance with this manual, the product content of the formulation must not decline by more than 10% when stored at room temperature over a period of two years.

We have found that this object is achieved by aqueous suspension concentrates which comprise
   a) 0.1–60% by weight of a tetrahydrophthalimide of the formula I,
   b) 0.1–30% by weight of an anionic surfactant,
   c) 0.1–30% by weight of a non-ionic surfactant,
   d) 0.01–5% by weight of a thixotroping additive,
   e) 0–50% by weight of other herbicidal active ingredients,
   f) 0–20% by weight of other formulation auxiliaries, and
   g) 1–90% of water.

The organic moieties mentioned in the definitions of B and R$^1$ to R$^6$ represent collective terms for individual enumerations of each of the meanings. All carbon chains, i.e. all alkyl, alkoxy, alkyloximino and alkoxyalkyl moieties, can be straight-chain or branched.

Examples of other meanings are:
   C$_1$–C$_6$-alkyl: methyl, ethyl, n-propyl, 1-methylethyl, n-butyl, 1-methylpropyl, 2-methylpropyl or 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl, n-propyl, 1-methylethyl, n-butyl, 1,1-dimethylethyl, n-pentyl or n-hexyl;
   (C$_1$–C$_6$-alkoxy)carbonyl: (C$_1$–C$_4$-alkoxy)carbonyl as mentioned above and, for example, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl, ethoxycarbonyl or 1-methylethoxycarbonyl;

($C_1$–$C_6$-alkoxy)carbonyl-$C_1$–$C_6$-alkoxy: $C_1$–$C_6$-alkoxy which is substituted by ($C_1$–$C_6$-alkoxy)carbonyl as mentioned above, i.e. for example methoxycarbonylmethoxy, ethoxycarbonylmethoxy, n-propoxycarbonylmethoxy, n-butoxycarbonylmethoxy, 1-(methoxycarbonyl)ethoxy, 2-(methoxycarbonyl)ethoxy, 2-(ethoxycarbonyl)ethoxy, 2-(n-propoxycarbonyl)ethoxy, 2-(n-butoxycarbonyl)ethoxy, 3-(methoxycarbonyl)propoxy, 3-(ethoxycarbonyl)propoxy, 3-(n-propoxycarbonyl)propoxy, 3-(n-butoxycarbonyl)propoxy, 4-(methoxycarbonyl)butoxy, 4-(ethoxycarbonyl)butoxy, 4-(n-propoxycarbonyl)butoxy, 4-(n-butoxycarbonyl)butoxy, 5-(methoxycarbonyl)pentoxy, 5-(ethoxycarbonyl)pentoxy, 5-(n-propoxycarbonyl)pentoxy, 5-(n-butoxycarbonyl)butoxy, 6-(methoxycarbonyl)hexoxy, 6-(ethoxycarbonyl)hexoxy, 6-(n-propoxycarbonyl)hexoxy or 6-(n-butoxycarbonyl)hexoxy, in particular methoxycarbonylmethoxy or 1-(methoxycarbonyl)ethoxy;

$C_1$–$C_6$-alkoxy: methoxy, ethoxy, n-propoxy, 1-methylethoxy, n-butoxy, 1-methylpropoxy, 2-methylpropoxy or 1,1-dimethyl-ethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, in particular methoxy, ethoxy or 1-methylethoxy;

$C_1$–$C_6$-alkoxy-$C_1$–$C_6$-alkyl: $C_1$–$C_6$-alkyl which is substituted by $C_1$–$C_6$-alkoxy as mentioned above, i.e. for example methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)-butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular methoxymethyl or 2-methoxyethyl;

$C_1$–$C_6$-alkyloximino-$C_1$–$C_6$-alkyl: $C_1$–$C_6$-alkyl which is substituted by $C_1$–$C_6$-alkyloximino such as methoxyimino, ethoxyimino, 1-propoxyimino, 2-propoxyimino, 1-methylethoxy-imino, n-butoxyimino, sec-butoxyimino, tert-butoxyimino, 1-methyl-1-propoxyimino, 2-methyl-1-propoxyimino, 1-methyl-2-propoxyimino, 2-methyl-2-propoxyimino, n-pentoxyimino, 2-pentoxyimino, 3-pentoxyimino, 4-pentoxyimino, 1-methyl-1-butoxyimino, 2-methyl-1-butoxyimino, 3-methyl-1-butoxyimino, 1-methyl-2-butoxyimino, 2-methyl-2-butoxyimino, 3-methyl-2-butoxyimino, 1-methyl-3-butoxyimino, 2-methyl-3-butoxyimino, 3-methyl-3-butoxyimino, 1,1-dimethyl-2-propoxyimino, 1,2-dimethyl-1-propoxyimino, 1,2-dimethyl-2-propoxyimino, 1-ethyl-1-propoxyimino, 1-ethyl-2-propoxyimino, n-hexoxyimino, 2-hexoxyimino, 3-hexoxyimino, 4-hexoxyimino, 5-hexoxyimino, 1-methyl-1-pentoxyimino, 2-methyl-1-pentoxyimino, 3-methyl-1-pentoxyimino, 4-methyl-1-pentoxyimino, 1-methyl-2-pentoxyimino, 2-methyl-2-pentoxyimino, 3-methyl-2-pentoxyimino, 4-methyl-2-pentoxyimino, 1-methyl-3-pentoxyimino, 2-methyl-3-pentoxyimino, 3-methyl-3-pentoxyimino, 4-methyl-3-pentoxyimino, 1-methyl-4-pentoxyimino, 2-methyl-4-pentoxyimino, 3-methyl-4-pentoxyimino, 4-methyl-4-pentoxyimino, 1,1-dimethyl-2-butoxyimino, 1,1-dimethyl-3-butoxyimino, 1,2-dimethyl-1-butoxyimino, 1,2-dimethyl-2-butoxyimino, 1,2-dimethyl-3-butoxyimino, 1,3-dimethyl-1-butoxyimino, 1,3-dimethyl-2-butoxyimino, 1,3-dimethyl-3-butoxyimino, 2,2-dimethyl-3-butoxyimino, 2,3-dimethyl-1-butoxyimino, 2,3-dimethyl-2-butoxyimino, 2,3-dimethyl-3-butoxyimino, 3,3-dimethyl-1-butoxyimino, 3,3-dimethyl-2-butoxyimino, 1-ethyl-1-butoxyimino, 1-ethyl-2-butoxyimino, 1-ethyl-3-butoxyimino, 2-ethyl-1-butoxyimino, 2-ethyl-2-butoxyimino, 2-ethyl-3-butoxyimino, 1,1,2-trimethyl-2-propoxyimino, 1-ethyl-1-methyl-2-propoxyimino, 1-ethyl-2-methyl-1-propoxyimino and 1-ethyl-2-methyl-2-propoxyimino, i.e. for example methoxyiminomethyl;

$C_3$–$C_8$-alkenyl: for example prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent- 3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl, in particular prop-2-en-1-yl or n-buten-4-yl;

$C_3$–$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, in particular prop-2-yn-1-yl;

$C_3$–$C_7$-cycloalkyl: cyclopropyl, cyclobutyl, cyclopentyl, cyclohexyl or cycloheptyl, in particular cyclopentyl or cyclohexyl.

The formulations according to the invention preferably comprise 5–60, in particular 5–50, % by weight of a tetrahydrophthalimide of the formula I. Preferred tetrahydrophthalimides are compounds of the formula I where $R^1$ is hydrogen or fluorine, $R^3$ is Cl and $R^2$ is A—CO—B, $OR^5$ (where $R^5$=$C_1$–$C_6$-alkyl, $C_2$–$C_8$-alkenyl or $C_3$–$C_7$-cycloalkyl) or $OCH_2COOR^5$ ($R^5$ is $C_1$–$C_6$-alkyl). Compounds I.1 to I.5 are especially preferred:

I.1: $R^1$=H, $R^3$=Cl, $R^2$=—CH=C(Cl)—$COOC_2H_5$ (common name: cinidon-ethyl, cf. EP-A 240 659)

I.2: $R^1$=F, $R^3$=Cl, $R^2$=$OCH_2$—$COOC_5H_{11}$ (common name: flumicloracpentyl)

I.3: $R^1$=F, $R^3$=Cl, $R^2$=O-cyclopentyl;

I.4: $R^1$=F, $R^3$=Cl, $R^2$=$OCH(CH_3)$—C≡CH (common name: flumipropyn)

I.5: N-(7-fluoro-3,4-dihydro-3-oxo-4-prop-2-ynyl-2H-1,4-benzoxazin-6-yl)cyclohex-1-ene-1,2-dicarboximide (common name: flumioxazin)

As component b), the formulations according to the invention comprise 0.1–30, preferably 0.3–15 and in particular 0.5–7, % by weight of an anionic surfactant.

Such anionic surfactants are known per se to those skilled in the art and have been described in the literature.

Examples of suitable ionic surfactants are alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleumsulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, lignin-sulfite waste liquor, including their alkali metal, alkaline earth metal, ammonium and amine salts, alkyl phosphates, quaternary ammonium compounds, amine oxides, betaines and mixtures of these.

Preferred substances are condensates of sulfonated naphthalenes or phenols with formaldehyde and, if appropriate, urea, these substances being in the form of water-soluble salts.

As component c), the aqueous storage-stable formulations according to the invention comprise 0.1 to 30, preferably 0.3–15 and in particular 0.5 to 7, % by weight of a non-ionic surfactant.

Examples of suitable non-ionic surfactants are alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers and mixtures of these, polyacrylates and acrylic acid graft copolymers.

Preferred substances are polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers and mixtures of these.

Preferred mixtures of ionic and non-ionic surfactants are condensates of sulfonated phenols with urea and formaldehyde, and polyethylene glycol/polypropylene glycol ether block copolymers.

Suitable thixotropic additives d) are compounds which impart a pseudoplastic flow behavior to the formulation, i.e. a high viscosity in the resting state and a low viscosity in the agitated state. The thixotroping additives amount to 0.01 to 5, preferably 0.05 to 3 and in particular 0.1 to 2, % by weight.

Examples of suitable compounds are polysaccharides such as Xanthan® gum, Kelzan® by Kelco or Rhodopol® 23 (Rhone Poulenc).

In addition to the essential components a) to d), the formulations according to the invention may additionally comprise other herbicidal active ingredients and other formulation auxiliaries.

Suitable as other herbicidal active ingredients are, in particular, the groups listed below:

e1: Amides such as propanil;

e2: Aminophosphoric acids such as bilanafos (bialaphos), buminafos, glufosinate-ammonium, glyphosate, sulfosate;

e3: Anilides such as thiafluamide;

e4: Aryloxyalkanoic acids such as 2,4-D, 2,4-DB, clomeprop, dichlorprop, dichlorprop-P, (2,4-DP-P), fluoroxypyr, MCPA, MCPB, mecoprop, mecoprop-P, napropamide, napropanilide, triclopyr;

e5: Benzoic acids such as chloramben and dicamba;

e6: Benzothiadiazinones such as bentazone;

e7: Bleachers such as clomazone (dimethazone), flurtamone, diflufenican, fluorochloridone, flupoxam, fluridone, pyrazolate, sulcotrione (chloro-mesulone) isoxaflutol and 2-(2'-chloro-3'-ethoxy-4'-ethylsulfonylbenzoyl)-4-methyl-cyclohexane-1,3-dione;

e8: Carbamates such as asulam, barbane, butylate, carbetamide, chlorbufam, chlorpropham, cycloate, desmedipham, di-allate, EPTC, esprocarb, molinate, orbencarb, pebulate, phenisopham, phenmedipham, propham, prosulfocarb, pyributicarb, sulf-allate (CDEC), terbucarb, thiobencarb (benthiocarb), tiocarbazil, tri-allate and vernolate;

e9: Quinolincarboxylic acids such as quinclorac and quinmerac;

e10: Chloroacetanilides such as acetochlor, alachlor, butachlor, butenachlor, diethatyl-ethyl, dimethachlor, dimethenamide (cf. also under category c2) metazachlor, metolachlor, pretilachlor, propachlor, prynachlor, terbuchlor, thenylchlor and xylachlor;

e11: Dinitroanilines such as benefin, butralin, dinitramin, ethalfluralin, fluchloralin, isopropalin, nitralin, oryzalin, pendimethalin, prodiamine, profluralin and trifluralin;

e12: Dinitrophenols such as bromofenoxim, dinoseb, dinoseb-acetate, dinoterb and DNOC;

e13: Diphenyl ethers such as acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen and oxyfluorfen;

e14: Ureas such as benzthiazuron, buturon, chlorbromuron, chloroxuron, chlortoluron, cumyluron, dibenzyluron, cycluron, dimefuron, diuron, dymron, ethidimuron, fenuron, fluormeturon, isoproturon, isouron, karbutilat, linuron, methabenzthiazuron, metobenzuron, metoxuron, monolinuron, monuron, neburon, siduron, tebuthiuron, trimeturon and difenuron;

e15: Imidazolinones such as imazamethapyr, imazapyr, imazaquin, imazethabenz-methyl (imazame), imazethapyr and imazamox;

e16: Oxadiazoles such as methazole, oxadiargyl and oxadiazone;

e17: Phenols such as bromoxynil and ioxynil;

e18: Phenoxypropionic esters such as clodinafop, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl and quizalofoptefuryl;

e19: Protoporphyrinogen IX oxydase inhibitors such as benzofenap, fluthiacet-methyl, pyrazoxyfen, sulfentrazone, thidiazimine, carfentrazone, azafenidin, oxadiazon and oxadiargyl;

e20: Pyridazines such as chloridazon, norflurazon and pyridate;

e21: Pyridinecarboxylic acids such as clopyralid and picloram;

e21: Sulfonamides such as flumetsulam, metosulam, cloransulam-methyl and diclosulam;

e22: Triazines such as ametryn, atrazine, aziprotryn, cyanazine, cyprazine, desmetryn, dimethamethryn, dipropetryn, eglinazine-ethyl, hexazinon, procyazine, prometon, prometryn, propazine, secbumeton, simazine, simetryn, terbumeton, terbutryn, terbutylazine, trietazine and dimesyflam;

e23: Triazinones such as ethiozin, metamitron and metribuzin;

e24: Uracils such as bromacil, lenacil and terbacil;

e25: Sulfonyl ureas such as amidosulfuron, azimsulfuron, bensulfuron-methyl, chlorimuron-ethyl, chlorsulfuron, chlorsulfoxim, cinosulfuron, cyclo-sulfamuron, ethametsulfuron-methyl, ethoxysulfuron, flazasulfuron, flupyrsulfuron, halosulfuron-methyl, imazosulfuron, metsulfuron-methyl, nicosulfuron, oxysulfuron, primisulfuron, prosulfuron, pyrazosulfuron-ethyl, rimsulfuron, sulfosulfuron, sulfometuron-methyl, thifensulfuron-methyl, triasulfuron, tribenuron-methyl and triflusulfuron-methyl;

e26: Dipyridylenes such as difenzoquat, diquat and paraquat.

Preferred other herbicides e) are: aryloxyalkanecarboxylic acids such as 2,4-D, 2,4-DB, CMPP, CMPP-P, dichlorprop, dichlorprop-P, MCPA, MCPB, the esters of these compounds, in particular the isopropyl, butyl and isooctyl esters, especially the 2-ethylhexyl esters, and also [(4-amino-3,5-dichloro-6-fluoro-2-pyridyl)oxy]acetic acid (fluroxypyr), dicamba, chlortoluron, carfentrazone-ethyl, isoproturon, difenuron, metoxuron, monolinuron, neburon, imazethabenz-methyl, bromoxynil, ioxynil, clodinafop, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofoptefuryl; flumetsulam, metosulam, cloransulam-methyl, diclosulam, atrazine, simazine, cyanazine, terbutryn, diflufenzopyr, amidosulfuron, chlorimuron, chlorsulfuron, halosulfuron, metsulfuron-methyl, primisulfuron, thifensulfuron, triasulfuran, tribenuron-methyl, prosulfuron, ethoxysulfuron, flupyrsulfuron, sulfosulfuron, N-[[[4-methoxy-6-(trifluoro-methyl)-1,3,5-triazin-2-yl]-amino]carbonyl]-2-(trifluoromethyl)benzenesulfonamide.

Very specially preferred other herbicides e) are: carfentrazone-ethyl, dimethenamid, 2,4-D, dicamba, fluoroxypyr, pendimethalin, isoproturon, chlortoluron, flupyrsulfuron, N-[[[4-methoxy-6-(trifluoromethyl)-1,3,5-triazin-2-yl]amino]-carbonyl]-2-(trifluoromethyl) benzenesulfonamide, metsulfuron-methyl, amidosulfuron, imazethabenz-methyl, metosulam, diflufenican, flurtamone and sulfosulfuron.

The other herbicides amount to 0 to 50, preferably 0 to 35 and in particular 1 to 30, % by weight of the formulations according to the invention, based on the total weight of the formulation.

If appropriate, one or more formulation auxiliaries f) may also be concomitantly used in the aqueous herbicide formulation according to the invention. Examples of suitable formulation auxiliaries are fillers, antifoams, bactericides and antifreeze agents. Solvents may also be added, but quantities should be kept as small as possible.

The following can be used as solvents: $C_1$–$C_6$-alcohols such as methanol, ethanol, propanol and hexanol; glycols such as ethylene glycol, propylene glycol and butylene glycol: glycol ethers such as alkylene glycol mono-$C_1$–$C_6$-alkyl ethers such as ethylene glycol monomethyl ether and ethylene glycol monoethyl ether, and aromatic solvents such as Solvesso 200 (by Exxon), fatty acid esters such as methyl oleate, vegetable oils such as soya oil, sunflower oil and rapeseed oil. The solvents generally amount to 0–20% by weight.

Suitable antifoams are, for example, silicone emulsions, long-chain alcohols, fatty acids, organofluorine compounds and mixtures of these.

Bactericides may be added to stabilize the aqueous fungicide formulation. Examples of suitable bactericides are Proxel® (by ICI), Nipacide® BIT 20 (by Thor Chemie), Kathon® MK, Acticide® (Rohm & Haas).

In general, the antifoams and bactericides amount to 0.1–5, preferably 0.1–2, % by weight in each case.

The formulation auxiliaries can be concomitantly used in the formulation of the crop protection agent in a concentration of 0 to 20% by weight. If they are a constituent of the formulation, 5 to 15% by weight has proved useful.

The aqueous formulations according to the invention can be prepared by processes for the preparation of aqueous suspension concentrates which are known per se to those skilled in the art and have been described in the literature, which is why more detailed information on the preparation can be dispensed with here.

The formulations according to the invention are used in the field of crop protection for controlling undesired plant growth (as herbicides).

The herbicidal formulations according to the invention can be applied pre- or post-emergence. If the active ingredients are less well tolerated for certain crop plants, application techniques can be used in which the herbicidal formulations are sprayed, with the aid of the spraying equipment, in such a way that the active ingredients come into as little contact as possible with the leaves of the sensitive crop plants while reaching the leaves of plants which grow underneath, or the bare soil (post-directed, lay-by).

To this end, the formulations according to the invention are diluted and then applied to the plants, preferably by means of foliar spraying. Application may be effected for example with water as the carrier, using customary spray techniques with amounts of approximately 100 to 1000 l of spray mixture per ha.

The compositions according to the invention can be employed at application rates of 0.001 to 5 kg/ha, preferably 0.01 to 3 kg/ha, in particular 0.01 to 0.6 kg/ha.

The examples which follow illustrate the subject of the invention. The tests described in the examples were carried out as follows:

The active ingredient content of the formulations was determined in each case by means of quantitative HPLC; it is indicated in grams per liter.

To test the storage stability, samples of the formulation in question are stored for a specific time in tightly sealed glass vessels at the temperature indicated in each case. The samples are subsequently examined and compared with the comparison value at the beginning of the storage (zero value). The active ingredient content is given as relative quantity based on the zero value (as a percentage).

The storage experiments were performed similarly to the CIPAC MT 46 method. In this method, the long-term stability of a product is estimated by short-term storage at elevated temperature.

The additives employed in the examples are described in Table 1 below.

| Name | Chemical name | Supplier |
| --- | --- | --- |
| Wettol ® D1 | phenolsulfonic acid/ formaldehyde condensate | BASF AG |
| Pluronic ®PE 10500 | EO/PO block copolymer | BASF AG |
| Antifoam SRE | Silicone oil emulsion | Wacker-Chemie |
| Kelzan ® | Polysaccharide | Kelco |
| Kathon ® MK | Bactericide | Rohm & Haas |

EXAMPLE 1:

504 g of active ingredient I.1 (technical grade, 99%), 20 g of Wettol® D1 by BASF, 30 g of Pluronic® PE 10500 by BASF AG, 2 g of Kelzan®, 1.4 g of Kathon® MK, 50 g of 1,2-propylene glycol and 5 g of silicone emulsion by Wacker were made up to 1 l with water and the mixture was subsequently ground in a ball mill to a particle size of 60% <2 microns (measured using a Cilas granulometer 715, by Cilas, Marcoussis, France).

EXAMPLE 2

A suspension concentrate was prepared as described in Example 1 using 213 g of I.1 (technical grade, 93.8%),
70 g of propylene glycol,
20 g of Wettol® D 1,
20 g of Pluronic® PE 10500,
5 g of silicone emulsion,
3 g of Kelzan® S and water to 1000 ml.

EXAMPLE 3

100 ml of the concentrate obtained in Example 1 were mixed with 2 l of a suspension concentrate comprising 400 g/l pendimethalin, using a propeller mixer. This gave a suspension concentrate (SC) comprising 24 g/l I.1 and 380 g/l pendimethalin.

EXAMPLE 4

100 ml of the concentrate obtained in Example 1 were mixed with 4 l of a concentrate comprising 300 g/l chlortoluron and 200 g/l pendimethalin, using a propeller mixer. This gave a suspension concentrate comprising 12 g/l I.1, 293 g/l chlortoluron and 195 g/l pendimethalin.

EXAMPLE 5

100 ml of the concentrate obtained in Example 1 were mixed with 2.5 l of a concentrate comprising 700 g/l chlortoluron, using a propeller mixer. This gave a suspension concentrate comprising 19 g/l I.1 and 673 g/l chlortoluron.

EXAMPLE 6

221 g of cinidon-ethyl (I.1) (technical grade, 95%), 355 g of N-[[[4-methoxy-6-(trifluoromethyl)-1,3,5-triazin-2-yl]amino]-carbonyl]-2-(trifluoromethyl)benzenesulfonamide (technical grade, 98%), 20 g of Wettol® D 1, 30 g of Pluronic® PE 10500, 5 g of silicone emulsion, 2 g of Kelzan® S, 1.8 g of Kathon® MK and 70 g of propylene glycol were made up to 1 l with water and ground to a particle size of 60% <2 µm using a ball mill (Dyno-Mill). This gave a suspension concentrate comprising 210 g/l cinidon-ethyl and 350 g/l N-[[[4-methoxy-6-(trifluoromethyl)-1,3,5-triazin-2-yl]amino)carbonyl]-2-(trifluoromethyl)benzenesulfonamide.

EXAMPLE 7

40 ml of the concentrate obtained in Example 1 were mixed with 1 l of a concentrate comprising 100 g/l diflufenican and 250 g/l flurtamone, using a propeller mixer. This gave a stable SC formulation.

The results from the storage-stability tests and the determination of the active ingredient contents can be seen from the table which follows:

| Example | Storage period | Temperature | Active ingredient content of I.1 |
|---|---|---|---|
| 1 | 30 d | 50° C. | 98% |
| 3 | 30 d | 50° C. | 98% |
| 4 | 30 d | 50° C. | 95% |
| 5 | 30 d | 50° C. | 90% |
| 6 | 14 d | 54° C. | 99% |

The results in the table show that the storage stability of the aqueous formulations according to the invention is very good.

What is claimed is:

1. A storage-stable aqueous formulation comprising
a) 0.1–60% by weight of a tetrahydrophthalimide of the formula I

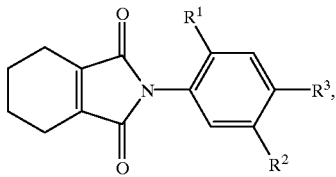

where the substituents have the following meanings:
$R^1$ is hydrogen, fluorine or chlorine;
$R^2$ is a group A—CO—B where A is CH=C(Cl) or CH=C(Br) and B is $C_1$–$C_6$-alkyl or a group $OR^4$ or $SR^4$ where $R^4$ is hydrogen, $C_1$–$C_4$-alkyl, ($C_1$–$C_6$-alkoxy)carbonyl-$C_1$–$C_6$-alkyl or $C_1$–$C_6$-alkyloximino-$C_1$–$C_6$-alkyl, or
$R^2$ is a group $OR^5$, $SR^5$, $COOR^5$ or $OCH_2COOR^5$ where $R^5$ is hydrogen, $C_1$–$C_6$-alkyl, $C_3$–$C_7$-cycloalkyl, $C_3$–$C_8$-alkenyl, $C_3$–$C_6$-alkynyl or $C_1$–$C_6$-alkoxy-$C_1$–$C_6$-alkyl, or
$R^2$ is a group $CH_2$—CO—$OR^6$ where $R^6$ is $C_1$–$C_6$-alkyl or $C_1$–$C_6$-alkoxy-$C_1$–$C_6$-alkyl, or
$R^2$ is a group —$NHSO_2$—($C_1$–$C_6$-alkyl) and
$R^3$ is chloro or cyano;
b) 0.1–30% by weight of an anionic surfactant,
c) 0.1–30% by weight of a non-ionic surfactant,
d) 0.01–5% by weight of a thixotroping additive,
e) 0–50% by weight of other herbicidal active ingredients,
f) 0–20% by weight of other formulation auxiliaries, and
g) 1–90% of water,
with the proviso that the sum of components a) to g) is 100% by weight.

2. A storage-stable aqueous formulation as claimed in claim 1 comprising, as component a), at least one of the active ingredients I.1. to I.5.:

I.1.: $R^1$=H, $R^3$=Cl, $R^2$=—CH=C(Cl)—$COOC_2H_5$
I.2.: $R^1$=F, $R^3$=Cl, $R^2$=$OCH_2$—$COOC_5H_{11}$
I.3.: $R^1$=F, $R^3$=Cl, $R^2$=O-cyclopentyl
I.4.: $R^1$=F, $R^3$=Cl, $R^2$=$OCH(CH_3)$—C≡CH
I.5.: N-(7-fluoro-3,4-dihydro-3-oxo-4-prop-2-ynyl-2H-1,4-benzoxazin-6-yl)cyclohex-1-ene-1,2-dicarboximide.

* * * * *